United States Patent [19]
Stemmann

[11] Patent Number: 5,425,763
[45] Date of Patent: Jun. 20, 1995

[54] MAGNET ARRANGEMENT FOR FASTENING PROSTHESES, IN PARTICULAR EPITHESES, SUCH AS FOR EXAMPLE ARTIFICIAL EARS AND THE LIKE

[76] Inventor: Hartmut Stemmann, Kollaustr. 6, D-22529 Hamburg, Germany

[21] Appl. No.: 112,533

[22] Filed: Aug. 27, 1993

[30] Foreign Application Priority Data

Aug. 27, 1992 [DE] Germany .................. 42 28 568.2

[51] Int. Cl.⁶ .......................... A61F 2/02; A61F 2/28
[52] U.S. Cl. ........................ 623/11; 623/16; 433/189; 403/DIG. 1; 335/285
[58] Field of Search ............ 623/12, 11, 15–16; 600/12; 403/DIG. 1; 433/189; 24/303; 335/285

[56] References Cited

U.S. PATENT DOCUMENTS

| | | | |
|---|---|---|---|
| 2,678,228 | 5/1954 | Gerhardt | 403/DIG. 1 X |
| 3,376,615 | 4/1968 | Heckman | 24/303 |
| 4,258,705 | 3/1981 | Sorensen et al. | 600/30 |
| 4,431,419 | 2/1984 | Portnoy | 433/189 |
| 4,824,371 | 4/1989 | Deutsch et al. | 433/189 |
| 4,997,372 | 3/1991 | Shiner et al. | 433/189 |
| 5,062,855 | 11/1991 | Rincoe | 623/24 |
| 5,072,750 | 12/1991 | Poms et al. | 403/DIG. 1 X |

FOREIGN PATENT DOCUMENTS

| | | | |
|---|---|---|---|
| 0347510 | 12/1989 | European Pat. Off. | |
| 2076270 | 10/1971 | France | |
| 2596274 | 10/1987 | France | 623/15 |
| 2820084 | 11/1978 | Germany | 433/189 |
| 0075124 | 4/1987 | Japan | 403/DIG. 1 |
| 1734724 | 5/1992 | U.S.S.R. | 623/12 |
| 8203547 | 10/1982 | WIPO | 433/189 |
| 8800814 | 2/1988 | WIPO | 623/15 |

Primary Examiner—David H. Willse
Attorney, Agent, or Firm—Burns, Doane, Swecker & Mathis

[57] ABSTRACT

In a magnet arrangement for the fastening of prostheses, in which a magnet which can be inserted into a prosthesis and a magnet to be implanted or to be fastened on an implant are provided, there is provided, to achieve a reliable mounting during a displacement movement of the prosthesis, a guide, by which the two magnets are guided on one another in such a manner that they are displaceable telescopically relative to one another in the holding direction of the prosthesis.

5 Claims, 4 Drawing Sheets

MAGNET ARRANGEMENT FOR FASTENING PROSTHESES, IN PARTICULAR EPITHESES, SUCH AS FOR EXAMPLE ARTIFICIAL EARS AND THE LIKE

BACKGROUND OF THE INVENTION

The invention relates to a magnet arrangement, adapted in particular to the physiological, biological and anatomical as well as muscular peculiarities on and in the human body, for fastening epitheses and obturators as well as other prostheses in and on the human body, such as for example artifical ears, noses, eyes, cheeks, chin, mouth and face parts, breasts, extremities and the like.

In medical history, various fastening devices between body replacement parts and intact body regions have become known. These include, in addition to endogenous tissue structures, external wire ligatures, bands, loops, implants and the like. Trials of a magnetic mounting have also been undertaken repeatedly. All these epithesis/body connections could not, however, bring about more than a rigid and thus unphysiological connection. Even the combinations, which have been used for some years, of enossally anchored titanium implants and rigid framework structures constructed thereon, on which the epitheses are then mounted via mechanical holding elements, do not produce the physiologically desired mobility. The safety of use necessary for the psychological well-being of the human being is thus also not achieved. In this manner, for example, in the case of considerable breathing-air compression, e.g. caused by sneezing, a nose epithesis or eye epithesis is forced off the previously conventional mechanical fastening, as a result of which embarrassing complications arise for the person concerned.

SUMMARY OF THE INVENTION

The object of the invention is to design a magnetic mounting for body replacement parts in such a manner that a mobility, which is adapted to the respective body region, of the body replacement part is present.

This object is achieved according to the invention. If, for example, in the fastening of an artificial ear, the musculature situated in the side head region contracts and in doing so swells as a result of pronounced facial and/or head movements, such as e.g. yawning, the development according to the invention prevents the ear epithesis falling off. By means of the development according to the invention, the artificial body replacement parts which have become necessary as a result of illnesses, injuries or deformities, can be connected to the intact body regions in a naturalness which was previously not possible, as a result of which the wearer of such body replacement parts is also afforded a high safety of use.

Previously, facial epitheses had additionally to be secured against falling off via a spectacle frame, this also only being possible to a limited extent. By means of the development of the magnetic fastening according to the invention, the supporting fastening by a spectacle frame can be omitted. A person wearing spectacles can thus use and remove the spectacles in an unhindered manner without impairing the epithesis fastening.

BRIEF DESCRIPTION OF THE DRAWINGS

Embodiments of the invention are by way of example explained in greater detail below with reference to the drawings, in which:

In FIG. 1, a circular-cylindrical prosthesis magnet 1 is surrounded by a titanium sleeve 2. The prosthesis magnet 1 and the titanium sleeve 2 are inserted into a hollow cylinder 3 made of iron which has a bottom part 4, against which the prosthesis magnet 1 bears. In the exemplary embodiment illustrated, the axial length of the iron cylinder 3 is more than twice the axial length of the prosthesis magnet 1 so that an edge section 5 of the iron cylinder 3 projects beyond the prosthesis magnet 1. This arrangement of prosthesis magnet 1, titanium sleeve 2 and iron cylinder 3 is surrounded on all sides by a gastight casing 6 made of titanium to form a magnetized section M1 which can be inserted into a prosthesis (not shown).

Figure 1:
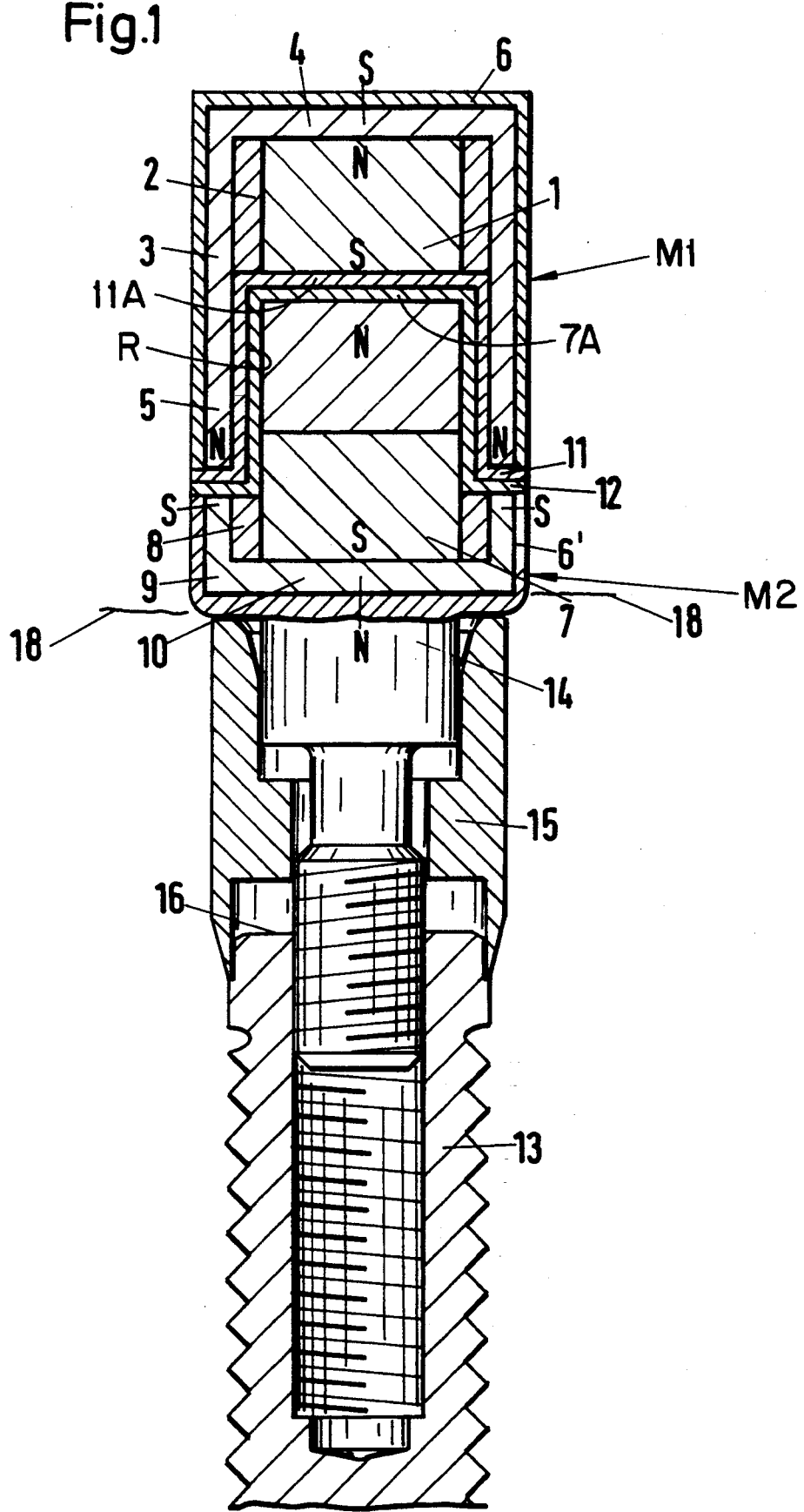
FIG. 1 shows a longitudinal section through a magnet arrangement with magnets bearing against one another.

A holding magnet is designated by 7, which in the exemplary embodiment illustrated consists of two superimposed circular-cylindrical magnet pieces so that the holding magnet 7 has an axial length which is approximately twice the axial length of the prosthesis magnet 1. The lower section of the holding magnet 7 is likewise surrounded by a titanium sleeve 8 and inserted with this into a hollow cylinder 9 made of iron which has a bottom part 10, against which the holding magnet 7 bears with the titanium sleeve 8. The height of the iron cylinder 9 is designed in such a manner that a longitudinal section of the holding magnet 7, corresponding to the free edge section 5, projects from the iron cylinder 9. This arrangement of holding magnet 7, titanium sleeve 8 and iron cylinder 9 is in turn surrounded on all sides by a gastight casing, 6' made of titanium to form another magnetized section 42.

The gastight casing 6 consists of a pot-shaped part and a cover 11 which is connected to the pot-shaped part in a gastight manner by welding by means of laser. The cover 11 covers the end side of the hollow cylinder 3, the inner circumference of the projecting edge section 5, and the end side of the prosthesis magnet 1 and titanium sleeve 2. The cover 12 of the casing 6' of the holding magnet 7 covers the projecting section of the holding magnet 7 and the end surfaces of the titanium sleeve 8 and the hollow cylinder 9 and engages positively in a recess R of the cover 11 in such a manner that the opposing cover surfaces bear against one another.

Figure 2:
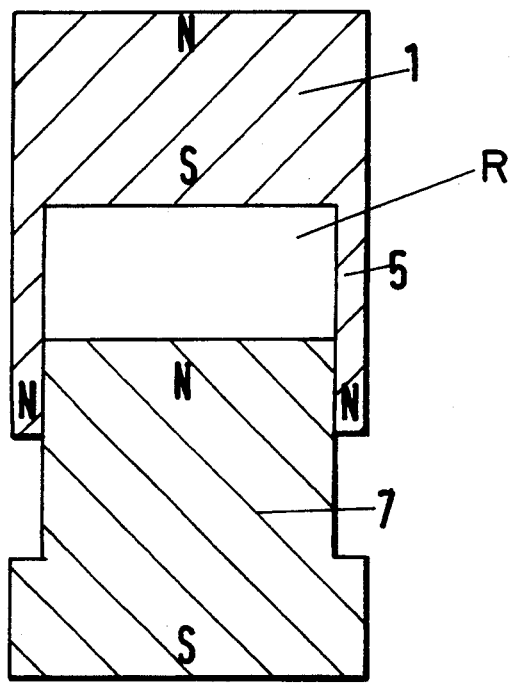
FIG. 2 shows a diagrammatic illustration of this magnet arrangement with magnets pulled apart.

The interlocking covers 11 and 12 form a guide for a telescopic displacement of the two magnets 1 and 7 relative to one another along the axis of the magnet arrangement or in the holding direction of the prosthesis, as can be seen from FIG. 2 which reproduces in simplified form the interlocking guide of the two magnets 1 and 7, the prosthesis magnet 1 being raised from the holding magnet 7.

In FIG. 1, 13 designates an implant which in a preceding operation has been implanted into the bone tissue (not shown). After a taking phase (ossification) lasting some months, this process is completed by the osseointegration of the implant, so that the epithetic or prosthetic care can begin.

Numeral 14 designates a part provided with a threaded shaft, which is screwed into the implant part 13. This part 14 provided with a thread can be protected with regard to the surrounding skin and muscle tissue with a distance sleeve 15 known per se. In FIG. 1, 18 indicates the skin surface. The holding magnet 7 or the casing 6 surrounding it is firmly connected to the part 14.

The cup-shaped iron cylinders 3 and 9 serve to shield the magnetic field on the prosthesis magnet 1 and on the holding magnet 7 to the outside. The titanium sleeves 2 and 8 serve as spacers between magnet and iron cylinder. Instead of titanium, it is also possible to use a physiologically and magnetically inert casting material such as cyanoacrylate. It is likewise possible to manufacture these distance sleeves 2 and 8 from Teflon or a Teflon-like material.

In the arrangement of the poles of the magnets 1 and 7 shown in FIGS. 1 and 2, there is on the bottom part 4 of the iron cylinder 3 a south pole S and on the projecting edge section 5 a north pole N. Correspondingly, as a result of the pole arrangement, there is on the holding magnet 7 a north pole N on the bottom part 10 of the iron cylinder 9 and a south pole S on the edge lying opposite the edge section 5. Thus, the inner portion of the recess R, formed by a floor 11A of the recess, is of polarity S, and the outer portion of the recess R is of polarity N. A free end 7A of a projecting portion of the magnetized section M2 which projects into the recess is of polarity N. That free end 7A is positioned opposite the floor 11A of the recess R when the projecting portion is fully inserted in the recess. Hence, the free end 7A is attracted by the floor 11A of the recess R and is repelled by the outer portion of the recess R in a direction toward the floor 11A.

If, for example as a result of a muscle distension in the environment of the implant 13, 14, the prosthesis is slightly raised, the prosthesis magnet 1—as FIG. 2 shows—is raised with the iron cylinder from the holding magnet 7, the projecting section of the holding magnet 7 being guided telescopically within the recess R. In this case, the north pole N of the holding magnet 7 comes to lie in the vicinity of the north pole N of the edge section 5 of the iron cylinder, so that, because of the repulsion of the two north poles, a damping of the displacement movement arises. By virtue of the fact that the north pole of the holding magnet 7 lies behind the north pole of the edge section 5, a force development of the holding effect which has been made more uniform arises during the telescopic displacement movement, so that the prosthesis is nevertheless not freed from the implant during a slight raising as a result of muscle distension.

If, in the case of muscle distension, for example upon laughing or yawning, a displacement path on an artificial ear of up to 2.8 mm has to be reckoned with, it is sufficient to design the telescopic guide by the edge section 5 and the projecting section of the holding magnet 7 for 3 mm, so that 0.2 mm still remains for the guide in the maximum displacement position. This is sufficient for a reliable mounting in the telescopic arrangement reproduced in FIGS. 1 and 2.

Figure 3:
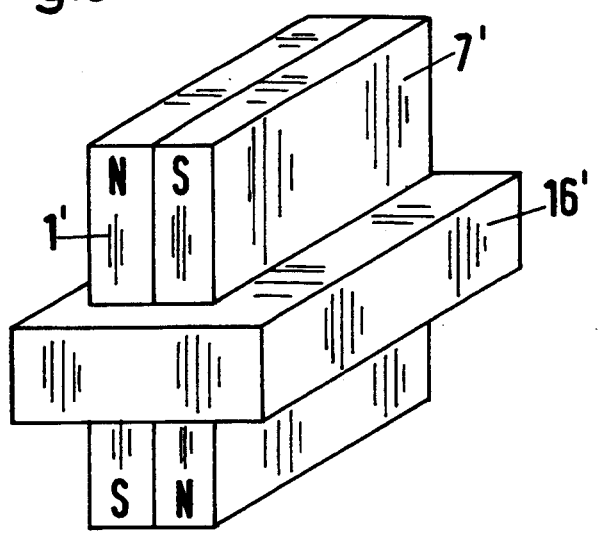
FIG. 3 shows in a perspective view a diagrammatic illustration of another exemplary embodiment.

Various modifications of the magnetic mounting with telescopic displacement of the magnets relative to one another are possible. FIG. 3 shows diagrammatically another embodiment of a magnetic mounting according to the invention, 16' reproducing diagrammatically a non-magnetic guide for two plate-shaped magnets 1' and 7', of which for example the magnet 1' is fastened on a prosthesis and the magnet 7' on an implant. By means of telescopic displacement of the two magnets 1' and 7' relative to one another, the north and south poles of the two magnets are moved away from one another and the like poles are moved towards one another, as a result of which a damping of the displacement movement is likewise produced.

Instead of the circular-cylindrical cross-sectional shape of the magnet arrangement according to FIGS. 1 and 2, a square or polygonal cross-sectional shape can be provided. It is likewise possible to have a bar-shaped magnet, for example the bar-shaped holding magnet 7, plunge into an annular prosthesis magnet 1. In this manner, a guide is formed by the magnetic parts, while in the embodiment according to FIG. 3 a non-magnetic separate guide 16' is provided.

It is also possible to design the prosthesis magnet 1 and the holding magnet 7, in the arrangement according to FIG. 1, in an annular manner, the iron cylinder surrounding the magnet projecting with a central section into the cavity in the annular magnet to concentrate the magnetic field.

The magnetic mounting described can be used for various prostheses and is suitable in particular for epitheses, for example artificial ears or artificial noses, in which a certain raising movement of the epithesis arises as a result of muscle movements, sneezing and the like. The magnetic mounting described guarantees a reliable mounting in spite of a certain raising movement of the epithesis.

Preferably, a circular-cylindrical telescopic arrangement of the magnetic mounting is provided, so that this magnetic mounting also allows turning in addition to a lifting movement. In this case, for mounting the epithesis, at least one further magnetic mounting is provided, in which the holding magnet has a spherical-surface-shaped end side which bears against a correspondingly concavely designed end side of the magnet inserted in the prosthesis or epithesis and allows a lateral deflection. Such a magnet arrangement is described in the European Patent Application 93 109 277.9.

While in the embodiment according to FIG. 1 a separate distance sleeve 15 is provided between the part 14 provided with the thread and the implant 13, a distance sleeve 17A, 17B, 17C, or 17D could be provided according to the invention, which is designed integrally with the casing 6A, 6B, 6C or 6D of the holding magnet 7 and various embodiments of which are reproduced in FIGS. 4A–4D. This distance sleeve, which is integrated with the magnet part, consists of titanium and is made in one piece with the gastight casing, the threaded shaft being welded into this distance sleeve 17.

The distance sleeve 17A–17D constitutes the outer screening to the epithelial passage point. The length of the distance sleeve is determined by the thickness of the muscle or epithelial (skin) tissue which is measured between the implant head designated by 16 in FIG. 1 and the skin surface 18. This distance sleeve 17A–17D made of biocompatible titanium facilitates for the treating doctor the screwing-in of the threaded shaft 14A, 14B, 14D with a force of 30 Ncm in the bleeding epithelial passage point, so that a firm seat of this insert is obtained. The operation area is already barely visible on the implant head 16 through the 3 to 8 mm thick epithelial tissue, and it is moreover covered by the bleeding. In the known distance sleeve 15 according to FIG. 1, the operating surgeon must first introduce the thread into the implant head 16, then mount the distance sleeve 15 flush on the implant head and finally tighten the thread. As a result of the development of the distance sleeve 17A, 17B, 17C, 17D according to FIGS. 4A–4D as an integral part with the titanium casing 6A–6D and the threaded shaft 14A, 14B, 14D, there is for the treating doctor a considerable simplification in the insertion with a simultaneous increase in the safety of use of the magnetic mounting.

Figure 4A:
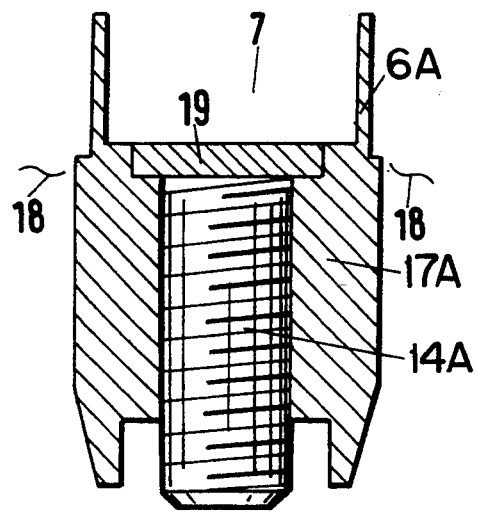
FIG. 4A–4D show various embodiments of a distance sleeve.
Figure 4B:
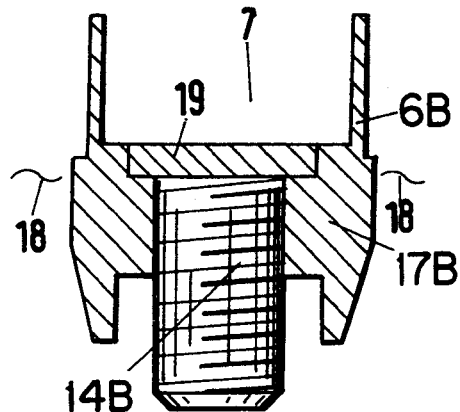
Figure 4C:
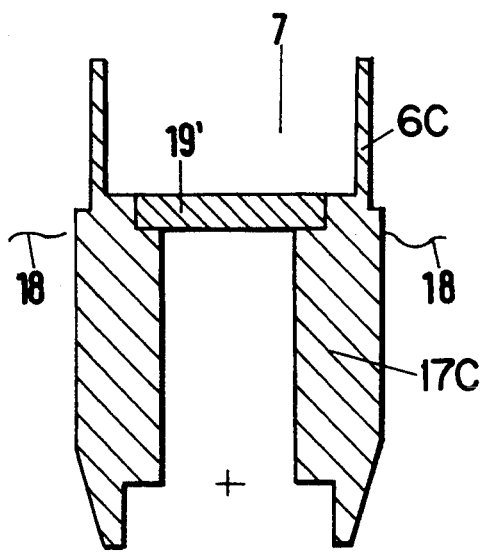
Figure 4D:
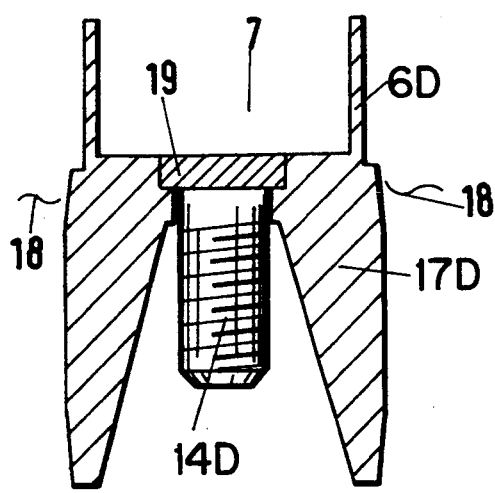

The shaping of the lower end of the distance sleeve is stipulated by the respective implant head 16 which is made by various manufacturers in various embodiments, as can be seen from a comparison of FIG. 4A and 4D. The threaded shaft must likewise be adapted to the respective implant head system. The length of the distance sleeve depends upon the thickness of the epithelium. FIG. 4A shows an embodiment with a long distance sleeve 17A of, for example, 8 mm, while FIG. 4B shows for the same implant a short distance sleeve 17B and short threaded shaft 14B for a thin skin part, which can, for example, be 1 mm long. The embodiment according to FIG. 4C is envisaged for an implant head of cylindrical design, on which the distance sleeve 17C is mounted and fastened by means of cement or adhesive. For covering the fastening point, a disc 19' is provided, which is welded into the distance sleeve 17C in a gastight manner by means of laser beams. The embodiment according to FIG. 4D involves a distance sleeve 17D for an implant head of conical design.

Expediently, there is formed on the threaded shaft 14A, 14B, 14C, which likewise consists of titanium, a disc or a flange 19 which is inserted into a corresponding heel of the inner bore of the distance sleeve 17A, 17B, 17D and, after adaptation to the implant part 13, is welded firmly by means of laser beams, so that the interior of the distance sleeve is closed off in a gastight manner.

Figure 5:
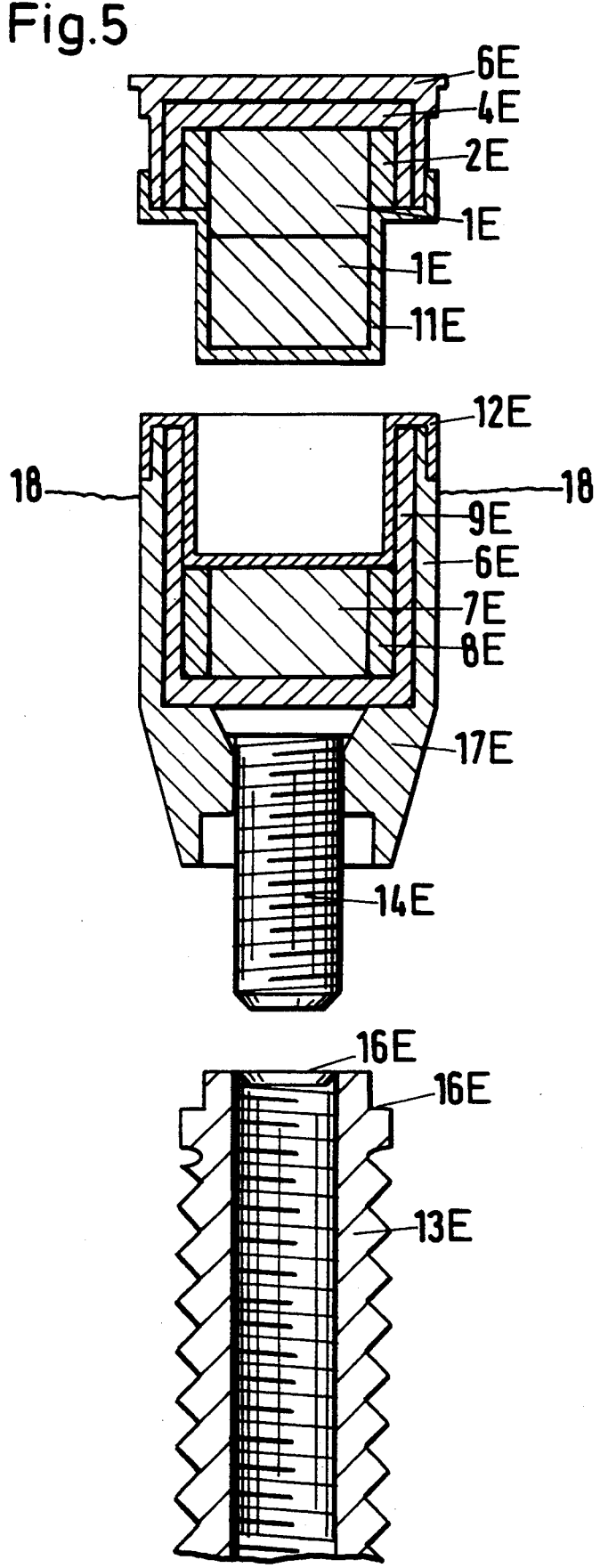
FIG. 5 shows a longitudinal section through another embodiment of a magnet arrangement, with the magnets pulled apart.

FIG. 5 shows an exploded view of an embodiment of the invention, wherein elements corresponding to those of FIG. 1 are provided with the same reference numeral with a suffix E. In contrast to FIG. 1E the prostheses magnet 1 is longer than the holding magnet 7E and engages in a cylindrical recess embodied at the structure of the holding magnet 7E. This embodiment elongated on the implant side is provided for a relatively thick mucous membrane 18 which covers the implant part 15E.

The cover 12E at the holding magnet 7E overlaps the upper edge of the casing 6E, which is integrally with the distance sleeve 17E (as in FIGS. 4A–4D), so that the line of weld for a gas-proof joint between cover 12E and casing 6E, which line of weld is formed by a laser beam, is at a distance from the upper edge on the outer circumference of the cylindrical structure.

In the same way the cover 11E on the prostheses magnet 1E is drawn over the edge of the casing 6E, which in this example of embodiment has a profiling for the insert in a prostheses not shown.

The distance sleeve 17E in FIG. 5 corresponds about to the one in FIG. 4B, wherein the casing 6E is elongated because of the thicker mucous membrane 18E and the head of the threaded shaft 14E is embodied cone-shaped.

The two magnets 1 (or 1E) and 7 (or 7E) in FIG. 1 and 5 can be embodied equally long as well, so that a shortening of the depth of immersion of the telescope structure results.

I claim:

1. A magnet system for fastening a prosthesis to a body, comprising a pair of magnetized sections connectible to the prosthesis and body, respectively; a first of said magnetized sections forming a recess having an inner portion and an outer portion; said inner portion comprising a floor of said recess and being magnetized with a first polarity; said outer portion being magnetized with a second polarity opposite said first polarity; a second of said magnetized sections including a projection disposed within said recess for inward and outward sliding movement therein; a free end of said projection being positioned opposite said floor and in contact therewith when said projection is fully inserted in said recess; said free end being magnetized with said second polarity so as to be normally magnetically attracted by said floor into contact therewith, and magnetically repelled by said outer portion of said recess in a direction toward said floor when said free end is moved out of contact with said floor.

2. The magnet system according to claim 1, wherein said first magnetized section comprises a first iron cylinder, and a first magnet disposed within a cylindrical interior of said first iron cylinder, said cylinder projecting beyond said first magnet in encompassing relationship with said recess.

3. The magnet system according to claim 2, wherein said second magnetized section comprises a second iron cylinder, and a second magnet disposed within a cylindrical interior of said second iron cylinder, said second magnet extending beyond said second iron cylinder and projecting into said recess.

4. The magnet system according to claim 1, wherein the one of said magnetized sections to be connected to the body includes a magnet disposed within a casing, said casing including an integral distance sleeve extending away from the other magnetized section.

5. The magnet system according to claim 4 including a threaded shaft disposed within said distance sleeve and adapted to be threadedly connected with an implant disposed in the body, a flange affixed to one end of said shaft and affixed within a recess disposed in said distance sleeve in a gastight manner.

* * * * *